(12) United States Patent
Baumann et al.

(10) Patent No.: US 11,300,775 B2
(45) Date of Patent: Apr. 12, 2022

(54) OBSERVATION INSTRUMENT AND A VIDEO IMAGER ARRANGEMENT THEREFOR

(71) Applicant: KARL STORZ SE & Co KG, Tuttlingen (DE)

(72) Inventors: Harald Baumann, Tuttlingen (DE); Peter Schwarz, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 57 days.

(21) Appl. No.: 16/872,513

(22) Filed: May 12, 2020

(65) Prior Publication Data

US 2020/0363625 A1   Nov. 19, 2020

(30) Foreign Application Priority Data

May 14, 2019   (DE) ..................... 10 2019 003 378.7

(51) Int. Cl.
*H04N 5/00*   (2011.01)
*G02B 23/00*   (2006.01)
(Continued)

(52) U.S. Cl.
CPC ....... *G02B 23/2484* (2013.01); *G02B 23/243* (2013.01); *H04N 5/2254* (2013.01); (Continued)

(58) Field of Classification Search
CPC ............. H04N 5/00; G02B 23/00; A61B 1/00
See application file for complete search history.

(56) References Cited

U.S. PATENT DOCUMENTS 4,598,980 A   7/1986 Doi
4,720,178 A   1/1988 Hishioka
(Continued)

FOREIGN PATENT DOCUMENTS

DE   102005015522 A1   10/2006
DE   102010028147 A1   10/2011
(Continued)

OTHER PUBLICATIONS

Gärtner, A., European Search Report, App 20173293.0, dated Oct. 2, 2020; pp. 1-6, Munich.
(Continued)

*Primary Examiner* — Maryam A Nasri
(74) *Attorney, Agent, or Firm* — Michael J. Loi; David Noel Villalpando

(57) ABSTRACT

An observation instrument has a shaft and an imaging unit, the imaging unit comprising an objective lens system and an electronic image sensor arranged for picking up an image generated by the objective lens system, the imaging unit being pivotably arranged in a distal end section of the shaft, a pivot axis of the imaging unit being transverse to a longitudinal axis of the distal end section of the shaft, wherein the image sensor is arranged substantially parallel to an optical axis of the objective lens system and the imaging unit comprises a deflection element for deflecting light exiting from an image end of the objective lens system to an image pick-up surface of the image sensor. The invention also relates to a video imager arrangement for an observation instrument.

14 Claims, 7 Drawing Sheets

(51) Int. Cl.
  *G02B 23/24* (2006.01)
  *H04N 5/225* (2006.01)
  *A61B 1/00* (2006.01)
  *A61B 1/05* (2006.01)

(52) U.S. Cl.
  CPC ....... *A61B 1/00096* (2013.01); *A61B 1/00183* (2013.01); *A61B 1/051* (2013.01); *H04N 2005/2255* (2013.01)

(56) References Cited

U.S. PATENT DOCUMENTS

| | | | |
|---|---|---|---|
| 4,746,203 | A | 5/1988 | Nishioka |
| 6,560,013 | B1 | 5/2003 | Ramsbottom |
| 6,801,370 | B2 | 10/2004 | Sekiyama |
| 7,553,277 | B2 | 6/2009 | Hoefig |
| 8,852,086 | B2 | 10/2014 | Pauli |
| 10,194,136 | B2 | 1/2019 | Schwarz |
| 2003/0092966 | A1 | 5/2003 | Schara et al. |
| 2010/0081875 | A1 | 4/2010 | Fowler et al. |
| 2014/0350338 | A1 | 11/2014 | Tanaka et al. |
| 2015/0238068 | A1 | 8/2015 | Rose et al. |
| 2015/0250380 | A1 | 9/2015 | Ikeda |
| 2015/0359420 | A1 | 12/2015 | Hatase et al. |
| 2016/0345805 | A1 | 12/2016 | Wieters et al. |
| 2018/0192857 | A1 | 7/2018 | Grant et al. |

FOREIGN PATENT DOCUMENTS

| | | | |
|---|---|---|---|
| DE | 102015003681 | A1 | 9/2016 |
| DE | 102017100056 | A1 | 7/2018 |
| EP | 1759629 | A1 | 8/2005 |
| JP | 07327916 | A | 12/1995 |
| JP | H07327916 | * | 12/1995 ............... A61B 1/00 |
| WO | WO2015/121145 | A1 | 8/2015 |

OTHER PUBLICATIONS

Knüfermann, P, German Search Report, Ap. 102019003378.7, dated Feb. 17, 2020, pp. 1-4, Munich.

* cited by examiner

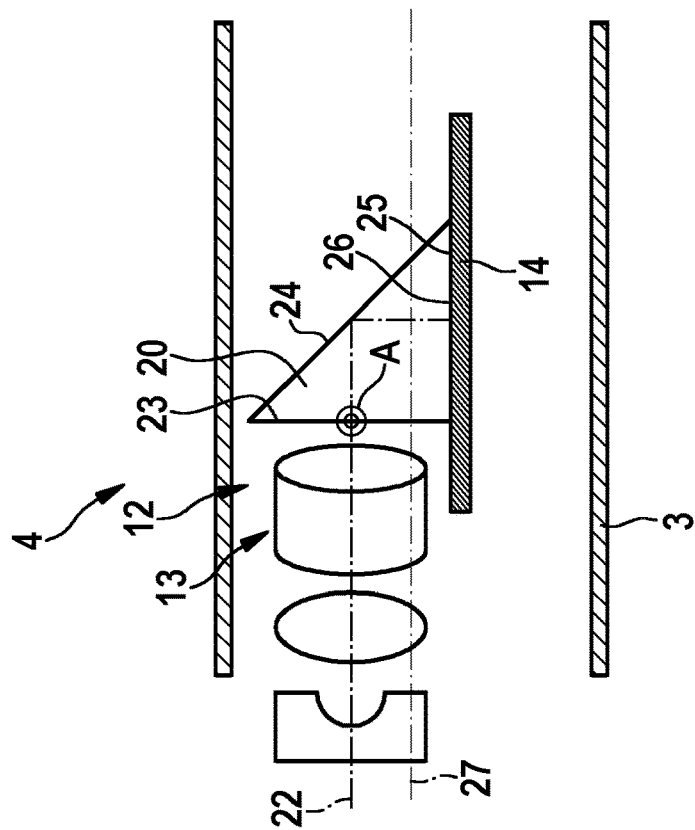
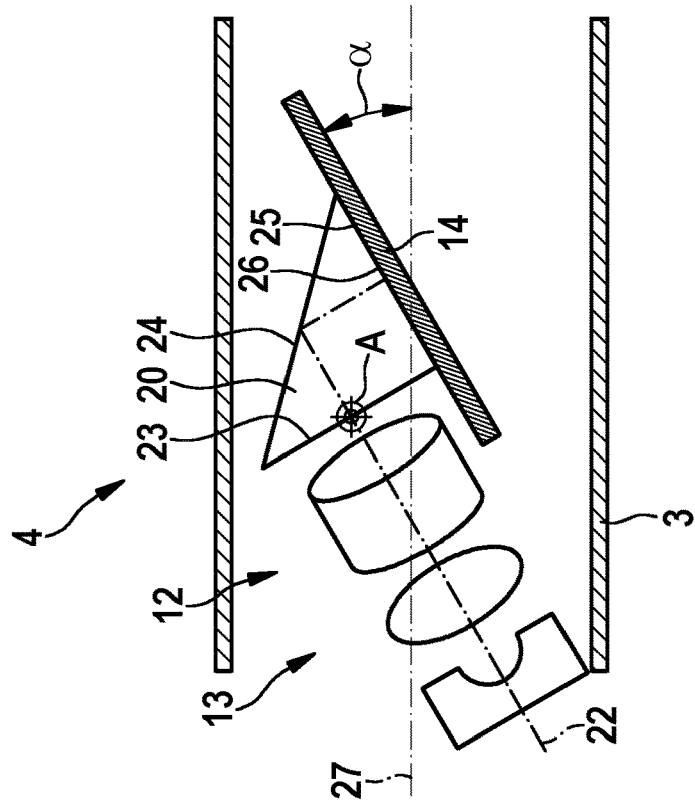

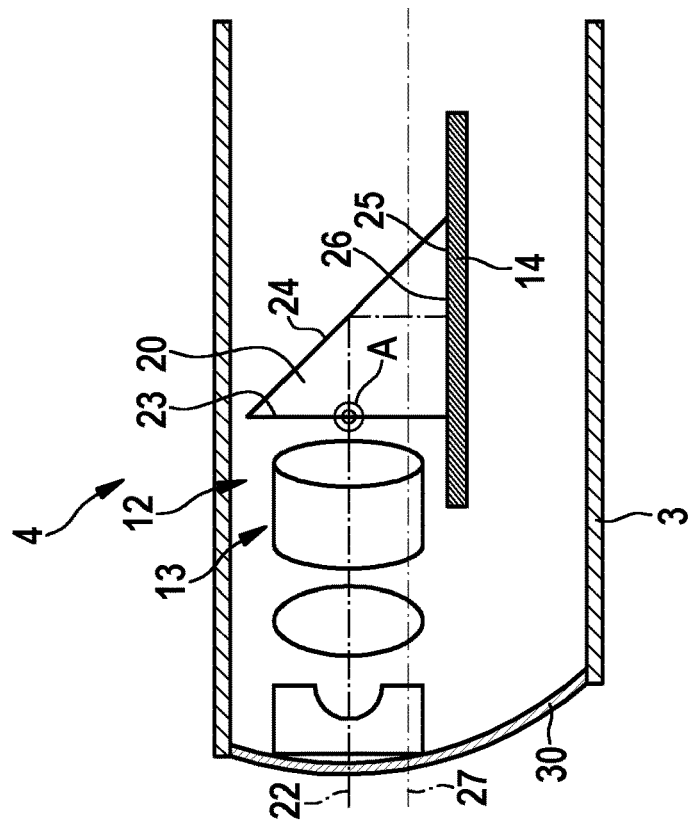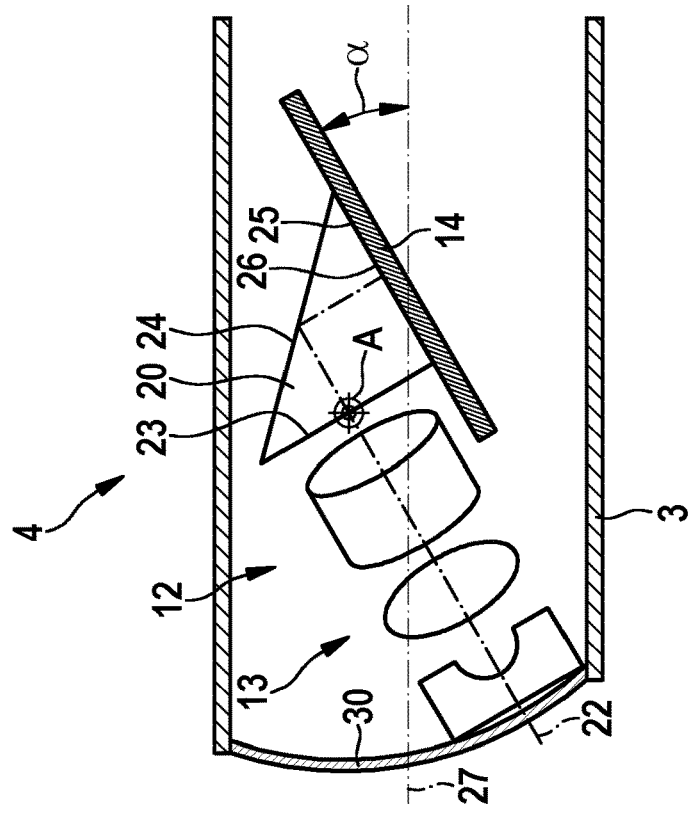

OBSERVATION INSTRUMENT AND A VIDEO IMAGER ARRANGEMENT THEREFOR

CROSS REFERENCE TO RELATED APPLICATIONS

This application claims priority to German Application No. 102019003378.7 filed May 14, 2019, entitled, "OBSERVATION INSTRUMENT AND VIDEO IMAGER ARRANGEMENT FOR AN OBSERVATION INSTRUMENT" and is incorporated herein by reference.

FIELD OF THE INVENTION

The present invention relates to an observation instrument, particularly one in the field of endoscopy, and to a distally placed video imager arrangement for such an observation instrument.

BACKGROUND OF THE INVENTION

Endoscopic examination techniques have prevailed in a multiplicity of medical and veterinary fields of application, as well as in many non-medical fields. In such examination techniques, an endoscope, which has an elongate shaft with an imaging optical system, is introduced into an internal cavity of a human or animal body or another object to be examined. The elongate shaft that is configured for being inserted into the cavity of the body or other object may be rigid, semi-rigid or flexible. In a distal (i.e. distant from an observer) end section of the elongate shaft an endoscope objective is arranged for generating in an image plane an image of an object field in the cavity of the body or object. In many endoscopes the generated image is picked up by an electronic image sensor arranged in the distal end section of the shaft and transmitted electronically towards a proximal (i.e. close to an observer) end section of the endoscope for being displayed to the observer.

Depending on an intended application, endoscopes with various viewing angles are known. In particular, oblique-view endoscopes are known which have a viewing direction that deviates from a longitudinal axis of the shaft. Moreover, optical observation instruments are known for observing a surgical field on a human or animal body from a position outside the body, which are designed with a shaft typically having an objective and an electronic image sensor in a distal end section of the shaft, being usually designed for oblique or side view. Such observation instruments are generally known as "exoscopes". Another kind of observation instrument is the endoscopic capsule that is designed for being introduced into a human or animal body and for being transported inside the body along a natural path, such as the intestinal tract or blood vessel, and which may comprise an objective and an electronic image sensor for capturing an image from inside the body and means for transmitting the captured image to the outside.

Frequently it is desirable for an observer to be able to adjust a direction of view provided by the observation instrument in order to observe different object fields within a body cavity, for example. To this end variable-direction-of-view endoscopes have been developed, which permit changing a direction of view defined by an optical assembly arranged at a distal end of an endoscope shaft. According to a common design principle, one or more optical deflection elements are provided adjacent to an objective lens system of the endoscope, being pivotably mounted for directing light entering into the system from a variety of viewing directions into an optical axis of the endoscope.

In WO 2015/121145 A1 an endoscope with a variable viewing direction is disclosed having a set of prisms, wherein a first prism can be pivoted with respect to a second prism about an axis of rotation. Due to the design principle, in such pivoting prism endoscopes only a limited opening angle of the field of view is achievable and, further, the optical imaging is not uniform over the entire swivel range, and therefore imaging errors such as astigmatism or distortion change with a variation of the direction of view.

According to US 2015/0359420 A1 an endoscope has a grip part and an insertion section which is inserted into a site to be observed. The insertion section has a straight portion and a bending portion, the bending portion having a rigid section at a tip end portion in which an imaging unit is accommodated. The imaging unit has an image pickup device and an optical lens that forms an image of object light on the image pickup device. The imaging unit is pivotally supported by a support arm, so as to be rotatable in a right-left direction.

As disclosed in US 2014/0350338 A1, an endoscope includes an insertion portion to be inserted into a subject to be observed, a first imaging unit and a second imaging unit arranged side by side in a distal end portion of the insertion portion. An optical axis of the first imaging unit can be changed to enable an image-capturing area of the first imaging unit to be moved along a direction in which the first imaging unit and the second imaging unit are arranged. The optical system of the first imaging unit is configured to have a wide angle of view. The image center of the first imaging unit has a resolution of 1920×1080 pixels (full HD).

DE 10 2015 003 681 A1 discloses a device for taking an image of an object field on a human or animal body from outside the body comprises a shaft and an optical unit arranged at a distal end of the shaft, which has observation optics for taking the image of the body Object field includes and which is rotatable about an at least approximately parallel to a viewing direction of the observation optics rotation axis, the observation optics having a first and a second stereo channel each having a lens and in each case at least one electronic image sensor.

According to DE 10 2017 100 056 A1 a video endoscope with a pivotable viewing direction comprises a handle with an operating element for pivoting the viewing direction, a shaft tube fastened to the handle distally with a viewing window which defines a hermetically sealed space extending into the handle, a control element movably mounted in a space between a housing wall of the handle and the hermetically sealed space to which a first magnetic coupling element is arranged, which interacts with a second magnetic coupling element arranged in the hermetically sealed space in such a way that the first and the second magnetic coupling elements comprise a magnetic coupling for contactless transmission to form rotational and/or translational movements.

BRIEF DESCRIPTION OF THE INVENTION

In prior art variable-direction-of-view video endoscopes having a pivotable imaging unit, the size of the electronic image sensor of the imaging unit is strictly limited by the available space inside the distal end section of the endoscope shaft. In particular, a diagonal of the image sensor must be less than an inner diameter of the distal end section of the shaft, so as to fit into the shaft in an orientation for providing a forward direction of view. However, the maximal achievable resolution depends on the dimensions of the image sensor, a larger image sensor in principle permitting increased resolution. On the other hand, the shaft diameter is limited by the application for which the endoscope is to be employed, for example by the diameter of a natural access to an internal body cavity.

It is an object of the present invention to provide an improved observation instrument, for example an endoscope, exoscope, or endoscopic capsule, with variable viewing direction. In particular, it is an object of the invention to provide an observation instrument having an electronic image sensor with an increased mechanical dimension, and thus permitting an increased resolution. Further, it is an object of the present invention to provide a video imager arrangement for an observation instrument in which an electronic image sensor with an increased size can be utilized.

In accordance with the present invention, an observation instrument has a shaft and an imaging unit. The observation instrument may be an endoscope, in particular a medical endoscope, being designed for medical applications, or a borescope, being designed for industrial or other non-medical applications. In the following, the observation instrument is described in terms of an endoscope, however it is to be understood that the observation instrument may be embodied as another kind of observation instrument, for example an exoscope or an endoscopic capsule, as is discussed below. The observation instrument may comprise further elements such as a handle comprising control elements and connections to external systems, and an illumination system for illuminating a cavity to be observed.

The shaft of the observation instrument, in particular in case of an endoscope, may be elongate and may be configured for being inserted into an internal cavity of a human or animal body or into some other hollow space in an object. The shaft may be formed by a substantially cylindrical tube, which may be rigid. In particular, a distal end section of the shaft may have an approximately cylindrical inner space.

The imaging unit comprises an objective lens system and an electronic image sensor that is arranged for picking up an image generated by the objective lens system. The objective lens system may comprise one or more lenses and other optical elements, such as an aperture stop, or plate element such as a filter, polarizer, retarder, or wave plate. The objective lens system is configured for collecting incoming light from an object field and to form an image of the object field in an image plane. The electronic image sensor may be, for example, a charge-coupled device (CCD) or a complementary metal-oxide semiconductor (CMOS). The image sensor includes a light-sensitive surface that serves as an image pick-up surface to receive the image generated by the objective lens system. The image sensor is configured to convert the captured image into an electrical image signal. The electrical image signal is transmitted to a storage and/or display unit for being stored and/or displayed to an observer. Electric lines, such as a cable or a flexible printed circuit board, may be provided extending along the shaft to a proximal end of the observation instrument in order to supply electric energy to the electronic image sensor and for transferring the image signal to the storage and/or display unit. The observation instrument may employ optical, infrared and/or ultraviolet radiation, which are all comprised by the term "light", for generating the image that is electronically picked up and transmitted for being displayed and/or stored.

The imaging unit is pivotably arranged in an end section of the shaft. In case of an endoscope, the imaging unit is pivotably held in a distal end section of the shaft. Thus, the objective lens system and the electronic image sensor can be pivoted with respect to the shaft while a relationship between the objective lens system and the electronic image sensor remains unchanged during the pivoting motion. In particular, the objective lens system and the image sensor may be fixed relative to each other within a frame or a housing of the imaging unit. The observation instrument may comprise an actuation mechanism such as a control wire operated from the proximal end of the instrument, or a motorized mechanism for controlling the pivoting motion of the imaging unit.

The pivoting of the objective lens system and the electronic image sensor with respect to the shaft allows a larger area to be viewed than with a fixed optic, such that the tip of the endoscope requires less physical movement by an operator.

A pivot axis of the pivotably arranged imaging unit, i.e. an axis about which the imaging unit can be pivoted, is substantially transverse to a longitudinal axis of the distal end section of the shaft. Preferably, the pivot axis forms an angle of about 90° to the longitudinal axis. Thus, the imaging unit can be tilted with respect to the distal end section of the shaft, the objective lens system forming variable angles to the longitudinal axis and therefore providing a variable direction of view. Upon operation of the actuation mechanism, a specific direction of view can thus be freely chosen within a certain range.

In accordance with the present invention, the image sensor is arranged substantially parallel to an optical axis or central axis of the objective lens system. In particular, the image sensor has a sensor plane that includes the light-sensitive surface or image pick-up surface, a normal to the sensor plane being substantially at a right angle to the optical axis of the objective lens system. For example, a normal on the sensor plane in a central area of the light-sensitive surface may intersect the optical axis at approximately 90°.

Further in accordance with the present invention, the imaging unit comprises a deflection element for deflecting light exiting from an image end of the objective lens system to the image pick-up surface of the image sensor. Light coming from an object field to be observed, having passed through the objective lens system and exiting from its image end is thus directed by the deflection element to the image pick-up surface of the image sensor. The deflection element is therefore configured and arranged such that the image generated by the objective lens system is formed on the image pick-up surface of the electronic image sensor, where it can be received to be converted into the electrical image signal. In particular, an axial light ray, i.e. a ray passing the objective lens system along or coaxial with the optical axis of the objective lens system, may be deflected by the deflection element towards the image pick-up surface. The image end of the objective lens system is also denoted "proximal end", while an opposing end, at which end the light coming from the object field enters into the objective lens system, is denoted "object end" or "distal end". The deflection element is arranged on the image side of the objective lens system in an optical path of the imaging unit between the objective lens system and the electronic image sensor. The deflection element is part of the pivotable imaging unit and is pivotable with respect to the shaft in conjunction with the objective lens system and the image sensor, its relation to the objective lens system and the electronic image sensor remaining substantially unchanged by the pivoting motion. The deflection element may have, in particular, a deflection angle of about 90°. Preferably, the objective lens system, the deflection element, and the image sensor are arranged such that the image plane of the objective lens system at least approximately coincides with the sensor plane of the image sensor, and the axial ray may be deflected such that it hits the sensor plane at or close to a central section of the light-sensitive area of the image sensor.

The observation instrument according to the present invention provides a variable direction of view, wherein the direction of view can be varied by pivoting the imaging unit, the objective lens system, the deflection element and the image sensor being comprised by the pivotable imaging unit. Due to the fixed relative arrangement of the objective lens system, the deflection element and the image sensor, image quality is independent of the chosen viewing angle, and, for example, distortion can be corrected for all viewing angles.

In a pivoting position of the imaging unit, in which the optical axis of the objective lens system is substantially parallel to the longitudinal axis of the distal end section of the shaft, i.e. in a straight-view position, the image sensor is arranged in an orientation that is substantially parallel to the longitudinal axis; such an arrangement may therefore be called a "lying" image sensor. Due to the "lying" arrangement of the image sensor, the dimensions of the image sensor are not strictly limited by a cross-section of the shaft, as it would be in a "standing" arrangement of the image sensor. Thus, a high-resolution image sensor having a rectangular shape with a longer and a shorter side can be integrated into the observation instrument shaft, even if a diagonal of the image sensor is longer than the inner width of the shaft, and thus the image sensor would be too large to fit into the shaft in a conventional arrangement. Moreover, generally, an objective lens system having a larger length generates an image having higher image quality than an image generated by a shorter objective lens system. Due to the objective lens system being arranged parallel to the longitudinal axis of the distal end section of the shaft in the straight-view position, the length of the objective lens system is not strictly limited by the inner width of the shaft. Thus, due to the arrangement in accordance with the present invention, high-quality optics and a high-resolution image sensor can be employed in an observation instrument having variable direction of view.

According to a preferred embodiment of the invention, the optical deflection element is a deflection prism that is arranged on the image pick-up surface of the image sensor and fixed to the image sensor, preferably rigidly fixed to the image sensor. In particular, the deflection prism has an entrance face, a deflection face and an exit face, the deflection face being at an angle of 45° to each of the entrance and exit faces, thus achieving a deflection angle of 90°. The deflection prism is preferably arranged having its exit face adjacent to the image pick-up surface of the image sensor. The exit face, in particular, has a size not less than a size of the image to be transmitted to the image pick-up surface of the image sensor, and preferably a length of the exit face, as measured parallel to the optical axis, exceeds the diameter of an image circle by not more than about 50%. The deflection prism may be glued with its exit face on the light-sensitive surface or on a cover glass of the light-sensitive surface of the image sensor. Further, a filter may be placed between the image pick-up surface and the exit face of the deflection prism. In this way, a compact and robust optical arrangement can be provided.

Preferably, the imaging unit comprises a sleeve holding the objective lens system, and the deflection element is a deflection prism fixed to an image end of the sleeve. In particular, the sleeve may have a tubular shape, lenses and other optical elements of the objective lens system being mounted inside the tubular sleeve. The deflection prism may be fixed rigidly to the sleeve, for example by mounting the sleeve to an entrance face of the deflection prism, or by mounting the deflection prism and the sleeve to a common frame or housing. According to a particularly preferred embodiment, the entrance face of the deflection prism is fixedly held adjacent to an image or proximal end of the sleeve, and the exit face is fixed to the image pick-up surface of the image sensor. Such an optical arrangement is particularly compact and robust, providing unchanged image quality independent of tilting angle.

Most preferably, the optical axis of the objective lens system is offset to a sensor plane of the electronic image sensor. The offset may depend on the dimensions of the objective lens system and of the deflection prism, which in turn may be related to the dimensions of the image generated on the image pick-up surface. For example, the offset may be about a diameter of the objective lens system, possibly including the sleeve. In this way a particularly simple optical design can be achieved, reducing production cost and optical losses.

According to a preferred embodiment, the pivot axis is arranged at a distal edge or in a distal end section of the electronic image sensor. Generally, electronic image sensors have an approximately rectangular shape having a shorter side and a longer side. Due to packaging and mechanical and electrical connections, the image sensor exceeds the size of the light-sensitive surface. In the present case, the image sensor may be arranged such that its shorter sides are approximately transverse to the longitudinal axis of the distal end section of the shaft. In a pivoting position in which the sensor plane is parallel to the longitudinal axis of the distal end section of the shaft, that one of the two edges forming the shorter sides of the image sensor that is closer to the distal end of the shaft is denoted the distal edge of the image sensor. In accordance with the present embodiment, the axis about which the imaging unit can be pivoted is located along or near the distal edge of the image sensor. The pivot axis may be defined mechanically by pivot points on opposing sides of a frame or housing of the imaging unit, interacting with corresponding bearings on an inner side of the shaft or in an inner structure of the shaft. Depending on the dimensions of the image sensor and the objective lens system, as well as depending on the available space in the distal end section of the shaft, an advantageous range of viewing directions can be achieved in this way.

Alternatively, the pivot axis may be arranged in a proximal end section of the objective lens system, i.e. at or near the image end of the objective lens system, or at or near the entrance face of the deflection prism. For example, the pivot axis may intersect the optical axis of the objective lens system at or near its image end. Such embodiments may be advantageous, depending on the dimensions of the image sensor and the objective lens system and depending on the available space in the distal end section of the shaft.

Due to the pivoting arrangement, the imaging unit is pivotable in a range of angular positions, defined by an angle the optical axis of the objective lens forms to the longitudinal axis of the distal end section of the shaft, which is a viewing angle of the observation instrument. In accordance with a preferred embodiment of the present invention, the imaging unit is pivotable between a first end position and a second end position, which end positions are the extreme angular positions limiting the pivoting motion of the imaging unit, in particular the angular positions defining a maximal or minimal viewing angle. Preferably, in the first end position the optical axis of the objective lens system is substantially parallel to the longitudinal axis of the distal end section of the shaft, and thus the viewing direction of the imaging unit is substantially parallel to the longitudinal axis of the distal end section of the shaft. In the second end position the optical axis forms a maximal angle to the longitudinal axis, defining a maximal viewing angle. At least the second end position, which corresponds to a maximal tilting angle of the imaging unit, may be defined by a mechanical stop. The viewing direction of the observation instrument can therefore be varied from a forward direction to a side-view direction by the pivoting motion to one side of the shaft axis within a range from 0° to the maximal viewing angle. Thus a maximal range of freely choosable viewing directions can be provided, wherein a further degree of freedom may consist in a rotation of the shaft about its longitudinal axis.

Most preferably, the maximal viewing angle is between 25° and 75°, i.e. the range of viewing directions of the observation instrument is from 0° to the maximal angle mentioned. Such a viewing angle corresponds to such a maximal tilting angle of the imaging unit that permits employing an advantageous imaging arrangement inside a small-diameter shaft, the arrangement comprising an image sensor with a considerably increased resolution and an objective lens system having high image quality. A maximal viewing angle between 25° and 75°, combined with a typical field of view, is sufficient for most endoscopic applications.

Preferably, the distal end section of the shaft has an approximately cylindrical inner space in which the imaging unit is arranged. Preferably, a length L of the objective lens system as defined by a distance between the object end and the image end of the objective lens system, satisfies the relation $$L \leq h/\sin\alpha - d/\tan\alpha.$$

wherein h is an inner diameter of the distal end section of the shaft, d is a diameter of the objective lens system, and a is the maximal viewing angle. The length L of the objective lens system typically is less than the upper limit given, due to the curvature of the cylindrical tube forming the distal end section of the shaft. In this way, an available inner space in the distal end section of the shaft can be optimally used to employ an objective lens system having a sufficient length for providing high image quality, and at the same time permitting a viewing angle sufficient for many applications.

As mentioned above, the imaging sensor may have a rectangular shape with shorter and longer sides, wherein due to packaging and mechanical and electrical connections the dimensions of the image sensor usually are larger than its image pick-up surface. In accordance with a particularly preferred embodiment, the length of a diagonal of the image sensor exceeds the inner diameter h of the cylindrical inner space of the distal end section of the shaft. In particular, the image sensor may be arranged such that its shorter sides are approximately transverse to the longitudinal axis of the distal end section of the shaft, wherein a length of a longer side may exceed the inner diameter h of the cylindrical inner space. This permits employing a high-resolution sensor in a narrow shaft, while still allowing some pivoting motion. In particular a high-resolution sensor can be used that is too large to fit into the shaft in a "standing" arrangement. Thus an observation instrument with a variable direction of view can be provided having an increased resolution.

Preferably, the distal end of the shaft is sealed on its distal side by a curved cover glass. The curved cover glass may be curved in one dimension only, for example as a cylindrical section or a circular arc about the pivot axis of the imaging unit, or in two dimensions, forming a section of a sphere about a center point on the pivot axis, for example. In this way a compact and robust design can be provided having an image quality independent from pivot angle.

The observation instrument may be embodied as an endoscope, which case has been described above. Preferably, the endoscope may be a rigid endoscope having a rigid shaft. Alternatively, the observation instrument may be embodied, for example, as an exoscope or an endoscopic capsule. In case of the endoscopic capsule, the term "shaft" is to be understood to mean a roughly cylindrical section of the endoscopic capsule thus defining a longitudinal axis, and the term "distal" means a side of the capsule to which endoscopic view is provided.

The present invention also relates to a video imager arrangement for an observation instrument having a shaft, for example for an endoscope, an exoscope, or an endoscopic capsule as mentioned before. The video imager arrangement comprises an imaging unit, the imaging unit comprising an objective lens system and an electronic image sensor arranged for picking up an image generated by the objective lens system, the imaging unit being pivotably mountable in a distal end section of the shaft, wherein a pivot axis of the imaging unit is approximately transverse to a longitudinal axis of the distal end section of the shaft. In accordance with the present invention, the image sensor is arranged substantially parallel to an optical axis of the objective lens system and the imaging unit comprises a deflection element being arranged for deflecting object light exiting from the objective lens system at an image end to an image pick-up surface of the image sensor. Thus, the video imager arrangement is configured such that the image of an object field is generated by the objective lens system on the image pick-up surface of the image sensor, the image pick-up surface being substantially parallel to the optical axis of the objective lens system. The imaging unit may comprise a frame or a housing to which the objective lens system, the image sensor and the deflection element are fixed, the frame or housing having a pivot axis or pivot points for being mounted pivotably in the shaft of the observation instrument. In particular, the observation instrument and the imaging unit may be configured as described above.

The features of the invention as mentioned above and as described below apply not only in the combinations mentioned but also in other combinations or alone, without leaving the scope of the present invention.

BRIEF DESCRIPTION OF THE DRAWINGS

Further aspects of the present invention will be apparent from the figures and from the description of particular embodiments that follows. The figures are given by way of illustration only, and thus are not limitative of the present invention. The index numbers used throughout attempt to convey uniformity as much as possible, while also permitting distinct reference thereto. Therefore, the numbering system employed is for the sake of simplicity and clarity and should not be considered limiting.

FIGS. 6a and 6b show an imager arrangement according to a third embodiment of the invention in its end positions.

FIGS. 7a and 7b show a variation of the third embodiment of the invention.

DETAILED DESCRIPTION OF THE INVENTION

Figure 1:
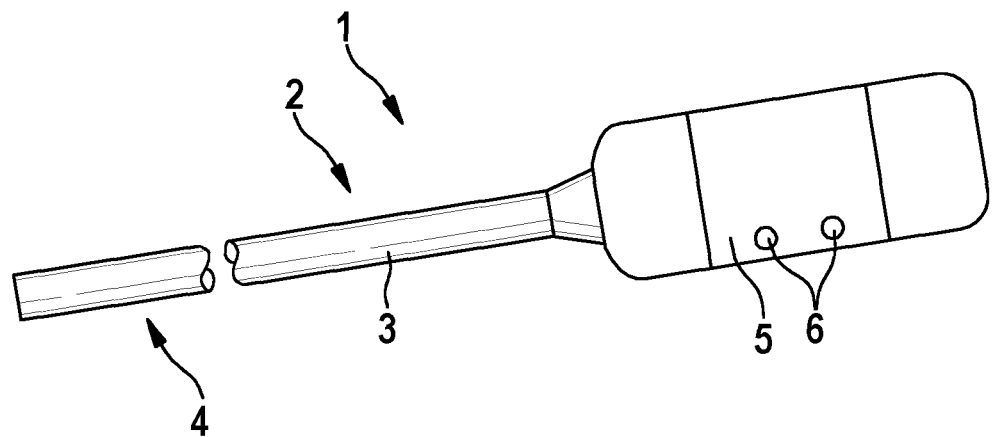
FIG. 1 shows an observation instrument in a schematic view.

As shown in FIG. 1, an observation instrument according to the invention may be embodied as a video endoscope 1. The video endoscope 1 comprises an elongate shaft 2 having a rigid tube 3 in the example shown; alternatively, the shaft could be semi-flexible or flexible. The distal end section of the shaft 2 is denoted with reference 4 in FIG. 1. The endoscope 1 further comprises a handpiece 5 arranged at a proximal end of the shaft 2. The handpiece 5 may comprise control elements 6 for controlling various functions of the endoscope 1, for example for controlling the viewing angle, and may comprise connections to electrical supply, image processing, display and/or storage means, as well as to an external light source (not shown).

Figure 2A:
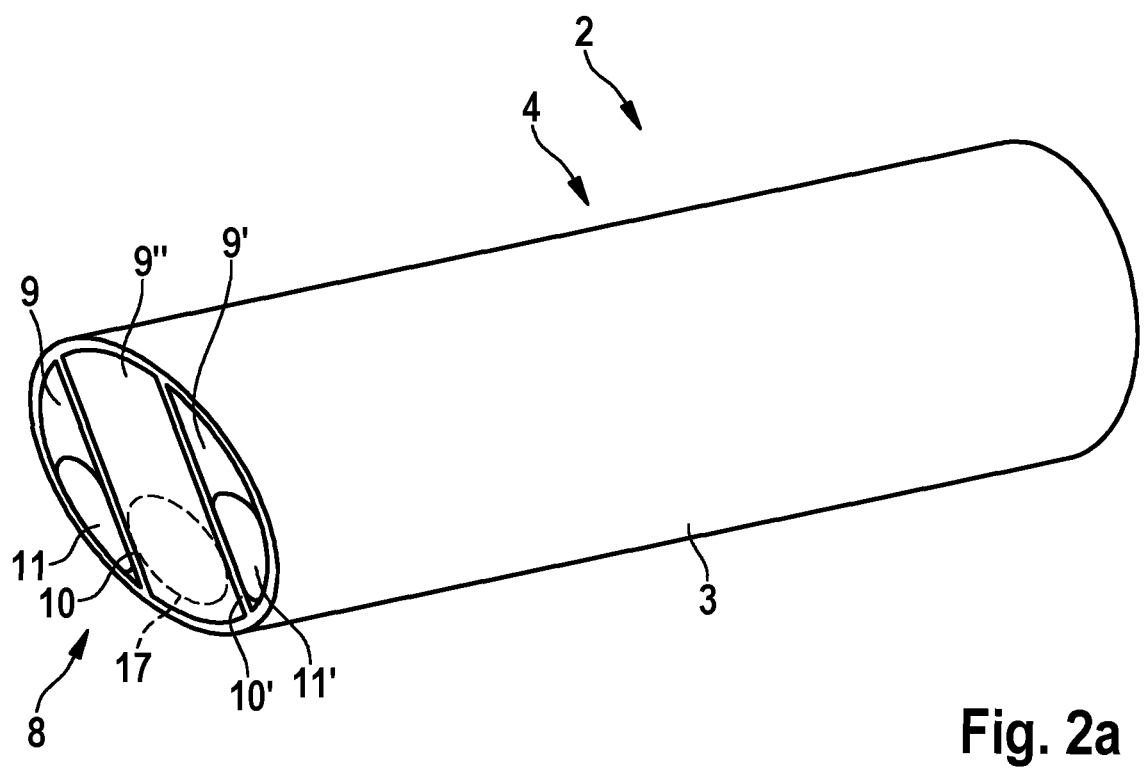
FIGS. 2a-2c show a distal end section of the observation instrument of FIG. 1 in accordance with a first embodiment of the invention in a perspective view, in a frontal view and in a sectional view, respectively.
Figure 2B:
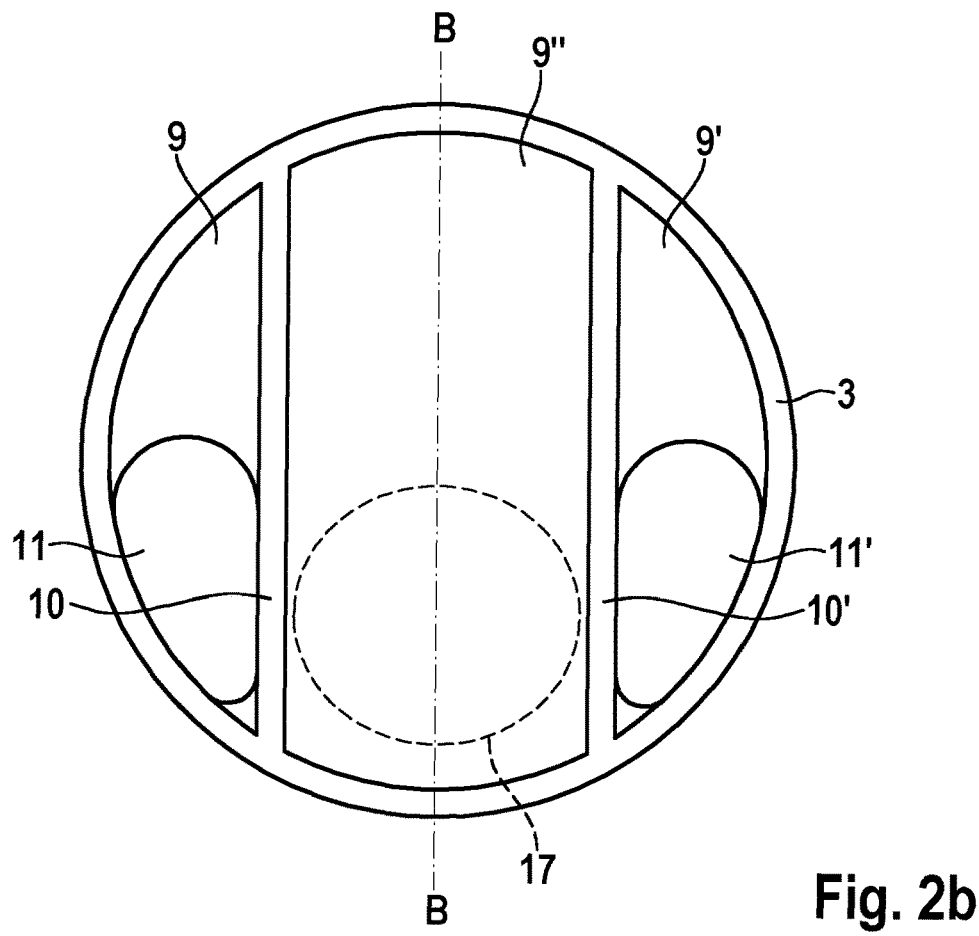
Figure 2C:
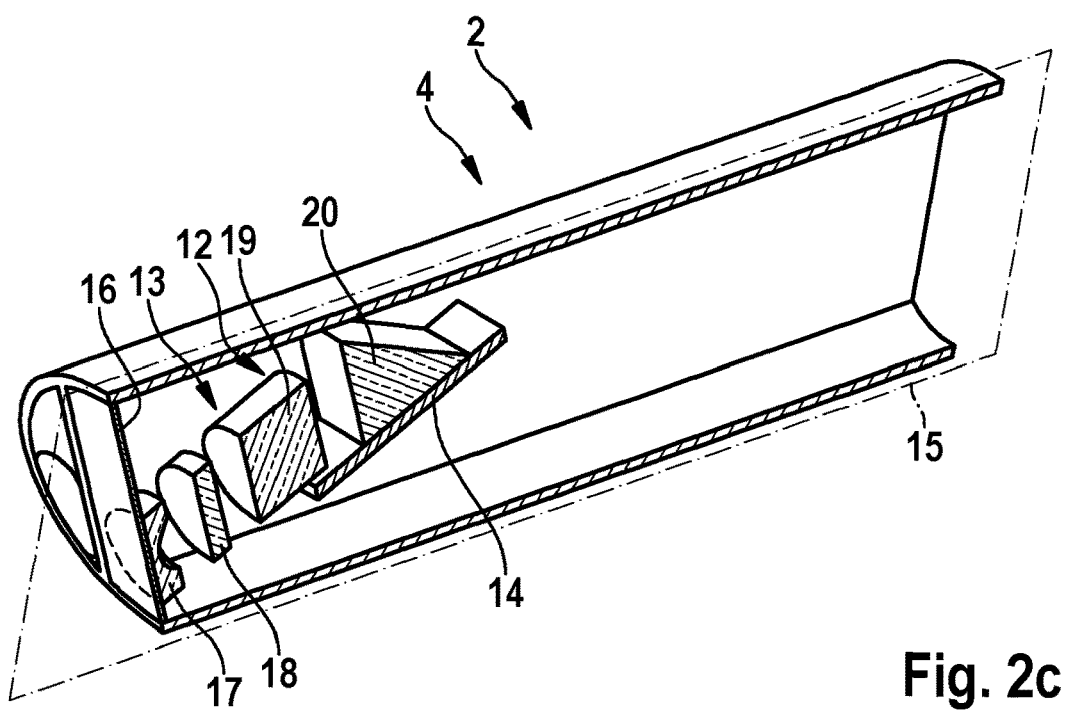

The distal end section 4 of the shaft 2 is shown in FIG. 2a in an enlarged perspective view, in FIG. 2b in an axial view seen from the distal side, and in FIG. 2c in a longitudinal sectional view. The shaft 2 has an oblique distal end 8. The distal end section 4 of the shaft 2 may have three internal compartments 9, 9', 9" separated by longitudinal walls 10, 10' inside the tube 3. In the side compartments 9, 9' light guides 11, 11' may be arranged for transmitting illumination light to the distal end 8 of the endoscope 1 and to illuminate an object field to be observed. The light guides 11, 11' may consist of a multiplicity of optical fibers that may be embedded at the distal end 8 in a suitable resin to form a hermetic seal.

The central compartment 9" comprises an imaging unit 12, which comprises an objective lens system 13 and an electronic image sensor 14 (see FIG. 2c). The sectional view shown in FIG. 2c is a section along line B-B in FIG. 2b in a longitudinal plane 15 of the distal end section 4 of the shaft 2. As described below, the imaging unit 12 is pivotably held in the distal end section 4. The central compartment 9" is hermetically sealed by a cover glass 16, which is transparent or is transparent at least in such sections which may be crossed by light rays that are imaged on the image sensor 14.

In the example shown the objective lens system 13 comprises at its distal end a negative front lens 17, and two further optical elements 18, 19, which may be imaging lenses. Typically the objective lens system 13 comprises one or more aperture stops (not shown). The lens 17 may be a single lens or a lens group, for example a cemented doublet or triplet. The further optical elements 18, 19 may be lenses and/or glass blocks, which in turn may be single optical elements or cemented doublets or triplets, for example. In the proximal direction following the objective lens system 13, the imaging unit 12 comprises a deflection prism 20 which is mounted on the image sensor 14. The deflection prism serves to deflect light rays exiting from the objective lens system 13 at its image end towards the image pick-up surface of the image sensor 14. The lens 17 of the objective lens system is indicated symbolically also in FIGS. 2a and 2b.

Figure 3:
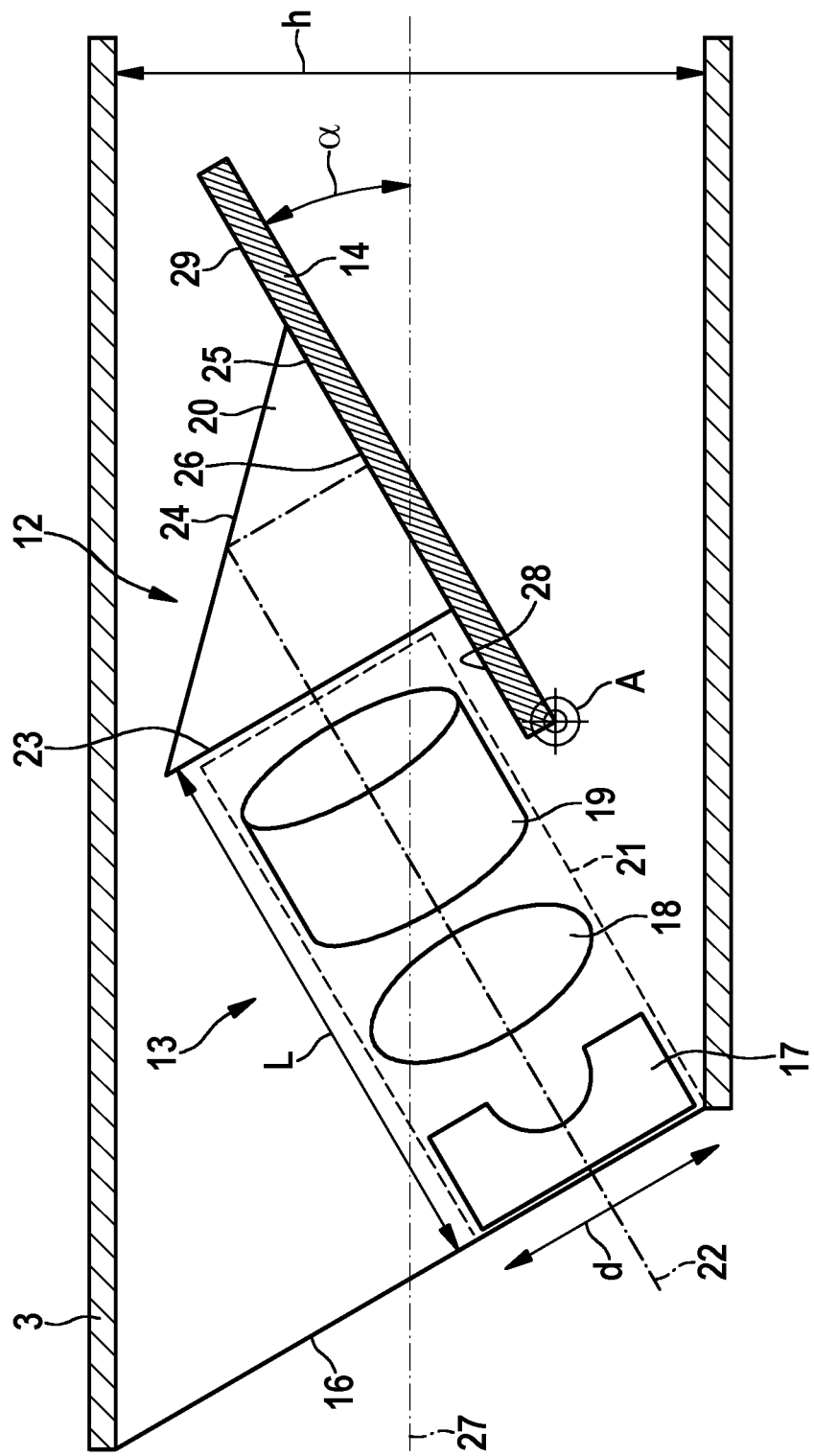
FIG. 3 shows the imager arrangement according to the first embodiment of the invention in a schematic view.

The imager arrangement according to a first embodiment of the present invention is shown in a schematic sectional view in FIG. 3. The imaging unit 12 is configured as shown in FIG. 2c and described above, while FIG. 3 shows further details. As indicated by dashed lines, the lens 17 and the further optical elements 18, 19 of the objective lens system are held in their respective positions by a sleeve 21 which is fixedly connected to the deflection prism 20 and the image sensor 14. The lens 17, the optical elements 18, 19, and the deflection prism 20 are configured such that rays entering the imaging unit 12 from an object field along or close to an optical axis 22, pass through the lens 17 and the optical elements 18, 19, enter into the deflection prism 20 at a right angle to an entrance face 23, are deflected by 90° at the deflection face 24 and exit from the deflection prism 20 at a right angle to an exit face 25. The deflection prism 20 is held on the image sensor 14 such that the exit face 25 is adjacent to an image pick-up surface 26 of the image sensor 14. For example, the deflection prism 20 may be fixed or glued with its exit face 25 to a cover glass of the image sensor 14 (not shown). The objective lens system 13 is configured to focus an image of an object field on the image pick-up surface 26, i.e. on the light-sensitive area of the image sensor 14, or at least on a part of the light-sensitive area. Due to the deflection at the deflection face 24 forming an angle of 45° to the image pick-up surface 26 of the image sensor 14, the optical axis 22 of the objective lens system 13 is substantially parallel to a sensor plane of the image sensor 14. The exit face 26 has a side length which at least equals the diameter of a circular image generated by the objective lens system 13 on the image pick-up surface 26, and preferably is less than about 150% of the image diameter.

Further, a pivot axis A of the imaging unit 12 is shown in FIG. 3, which may be, for example, configured as a bolt which is rotatably held in corresponding bearings in the walls 10, 10' (see FIG. 2b). The pivot axis A is substantially perpendicular to a longitudinal axis 27 of the distal end section 4. Thus, the imaging unit 12, comprising the objective lens system 13, the deflection prism 20 and the image sensor 14, is pivotably held in the distal end section 4 of the shaft 2, forming a substantially rigid unit pivotable about pivot axis A. The cover glass 16 is depicted only symbolically in FIG. 3. The imaging unit 12 may comprise further elements, such as one or more diaphragms and/or spacers (not shown). Moreover, one or more actuation elements may be provided for actuating the pivoting motion, such as a control wire connected to the control elements 6 of the handpiece 5 (see FIG. 1), which actuation elements are not shown in FIG. 3.

In the example depicted in FIG. 3, the pivot axis A is located at a distal edge of the approximately rectangular image sensor 14. As indicated in FIG. 3, the sleeve 21 holding the objective lens system 13 has a length L and a width d. This means that the imaging unit 12 can be pivoted up to a tilting angle α, in which position the relation is satisfied $$L \sin \alpha + d \cos \alpha \leq h$$

wherein h is the inner width of the tube 3 in the distal end section 4 of the shaft 2 (see FIG. 1). As is indicated in FIG. 3, the total height h may not be completely exploited due to the curvature of a cross-section of the tube 3 in the central compartment 9" (see FIG. 2b). Thus, generally $$L \sin \alpha + d \cos \alpha \leq h$$

If, on the other hand, the maximal tilting angle α is predefined, the maximal allowable length L of the objective lens system 13 is $$L \leq h/\sin\alpha - d/\tan\alpha$$

the maximal tilting angle α is the maximal angular deviation of the optical axis 22 of the objective lens system 13 from the longitudinal axis 27 of the distal end section 4 of the shaft 2, and thus the maximal viewing angle of the endoscope 1. The cover glass 16 is inclined correspondingly at an angle α with respect to a direction perpendicular to the longitudinal axis 27. The cover glass 16 may be substantially flat, as shown in FIGS. 2a, 2c, and 3, or the cover glass may be curved (see below).

Further, as can be seen in FIG. 3, the length of the longer side, or at least a length of a diagonal of the image sensor 14, can be larger than h, i.e. larger than the inner width of the tube 3, and may be larger than shown in FIG. 3. In standard image sensors, the dimensions of the image sensor 14 exceed the respective dimensions of the light-sensitive surface, and thus of the image pick-up surface 26, the image sensor 14 comprising margins for electrical connections and/or due to packaging. In FIG. 3 such margins 28, 29 are those parts of the surface of the image sensor that exceed the image pick-up surface 26. The exit face 25 of the deflection prism 20 substantially covers the image pick-up surface 26 and extends only over a small faction part of the margins 28, 29. A width of the image sensor 14, as well as the diameter of the sleeve 21 and the width of the deflection prism 20 are slightly less than a width of the central compartment 9" (see FIGS. 2a-2c).

As can also be seen in FIG. 3, in a shaft 2 of given inner height h the maximal achievable tilting angle α may be larger if L and/or the length of the image sensor 14 is smaller. Further, the smaller the image pick-up surface 26 is, the smaller the size of the deflection prism 20 can be chosen, which in turn permits choosing a smaller diameter d of the objective lens system 13 and thus permitting a larger maximal viewing angle α. Thus, if h is pre-defined, there may be a trade-off between L and/or d on the one hand and a on the other hand.

Figure 4B:
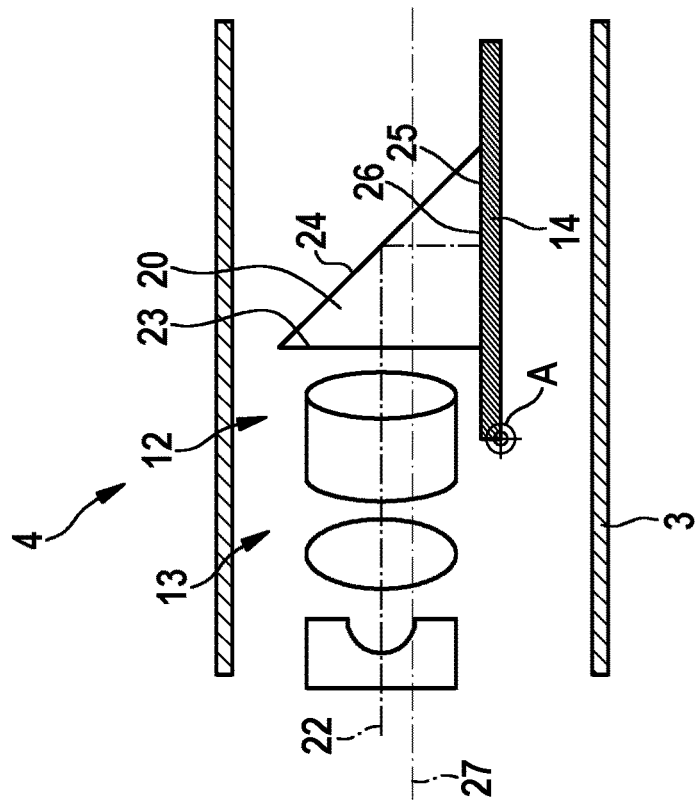
FIGS. 4a and 4b show the imager arrangement of FIG. 3 in its end positions.
Figure 4A:
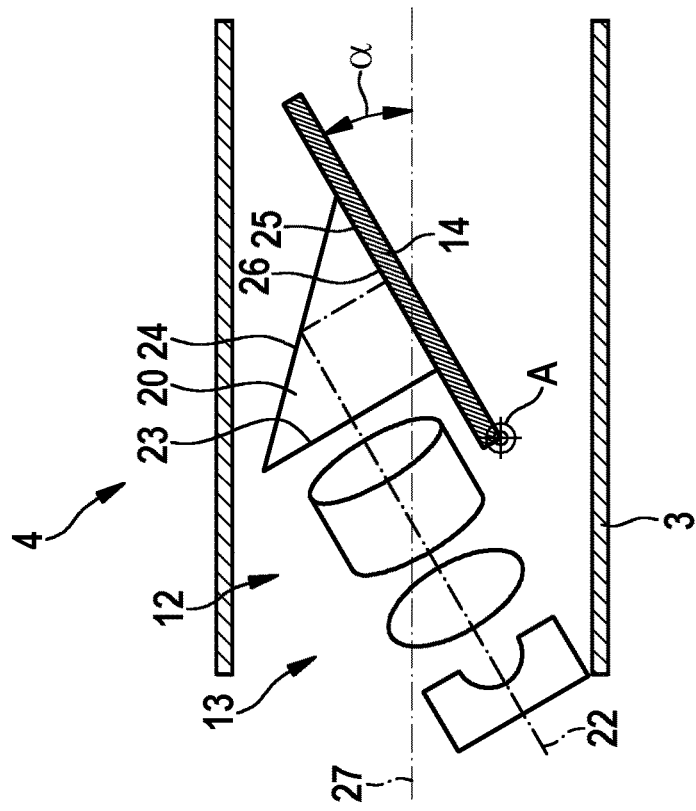

The imager arrangement of FIG. 3 is shown in its end positions in FIGS. 4a and 4b. The end position that corresponds to the maximal viewing angle or tilting angle α is shown in FIG. 4a, which is a simplified depiction of the situation of FIG. 3. FIG. 4b shows the minimal viewing angle, which is approximately 0°, i.e. a viewing direction parallel to the longitudinal axis 27 of the distal end section 4.

Figure 5B:
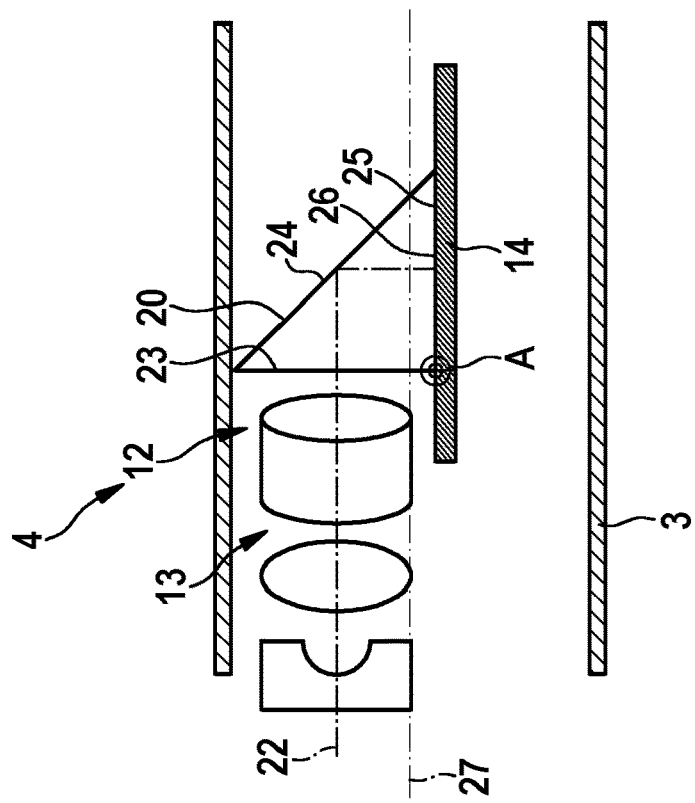
FIGS. 5a and 5b show an imager arrangement according to a second embodiment of the invention in its end positions.
Figure 5A:
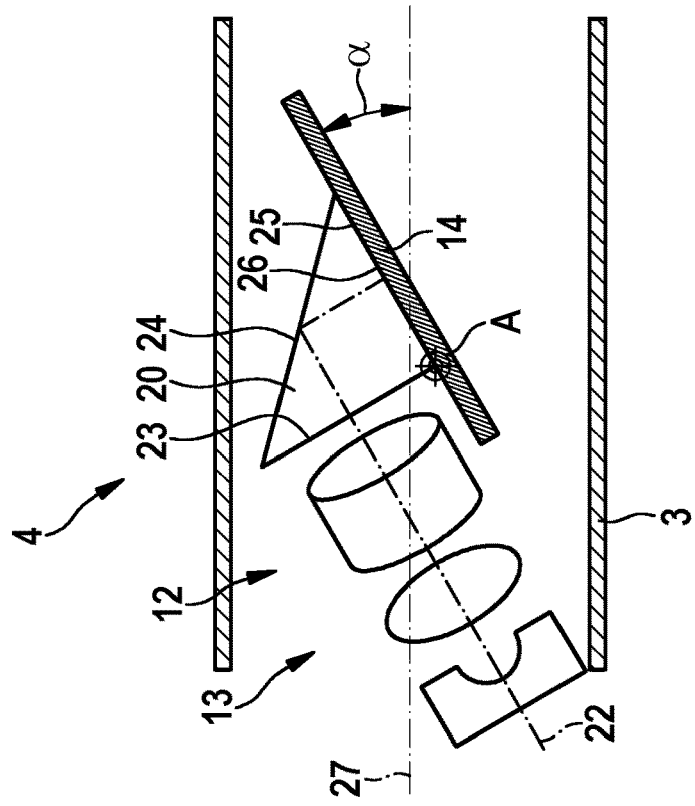

FIGS. 5a and 5b, as well as FIGS. 6a and 6b, show two alternative embodiments, which are distinguished from the arrangement of FIGS. 3 and 4a and 4b in differing locations of the pivot axis A. According to the embodiment of FIGS. 5a and 5b, the pivot axis A is located at the distal edge of the image pick-up surface 26, which approximately coincides with the intersection line of the entrance face 23 and the exit face 25 of the deflection prism 20. In the embodiment of FIGS. 6a and 6b, the pivot axis A is placed at a location that is defined by the intersection of the optical axis 22 of the objective lens system 13 with the entrance face 23 of the deflection prism 20, the pivot axis A being parallel to the image pick-up surface 26.

In a variation of the embodiment of FIGS. 6a and 6b and as depicted in FIGS. 7a and 7b, the tube 3 or at least the central compartment 9" may be sealed by a curved cover glass 30. The cover glass 30 may be curved in a circular arc about the pivot axis A, such that it is intersected perpendicularly by the optical axis 22 of the objective lens system at the end positions of the imaging unit 12 as shown in FIGS. 7a and 7b, and preferably at all possible viewing angles. The curved cover glass 30, on the other hand, may be embodied as a section of a sphere having its center of curvature on the pivot axis A, or may be curved in a shape that is not symmetrical with respect to the pivot axis A. Although a curved cover glass 30 is shown only in a variation of the third embodiment, a curved cover glass may be provided in corresponding variations of the other embodiments.

The three embodiments described differ in the maximal allowable length of the image sensor 14, which may exceed the length shown in the Figures on a distal and/or proximal side. In FIGS. 4a-6b the components of the imaging unit 12 and of the distal end section 4 of the shaft 2 are shown only symbolically.

According to the embodiments described, for example, a full HD sensor having 1.4 μm pixel size, and an objective lens system 13 having a corresponding diameter d of about 3 mm may be employed in a variable-direction-of-view endoscope having a shaft inner height h of about 5 mm, while the direction of view may be freely chosen in a total range of viewing angles up to a maximal viewing angle α of at least 25°.

For clarity not all reference numerals are displayed in all figures. If a reference numeral is not explicitly mentioned in the description of a figure, it has the same meaning as in the other figures.

REFERENCE NUMERALS

1 Endoscope
2 Shaft
3 Tube
4 Distal end section
5 Handpiece
6 Control element
8 Distal end
9, 9', 9" Compartment
10, 10' Wall
11, 11' Light guide
12 Imaging unit
13 Objective lens system
14 Image sensor
15 Plane
16 Cover glass
17 Lens
18 Optical element
19 Optical element
20 Deflection prism
21 Sleeve
22 Optical axis
23 Entrance face
24 Deflection face
25 Exit face
26 Image pick-up surface
27 Longitudinal axis
28 Margin
29 Margin
30 Cover glass
A Pivot axis

The invention claimed is:

1. An observation instrument comprising a shaft and an imaging unit, the imaging unit comprising an objective lens system and an electronic image sensor arranged for picking up an image generated by the objective lens system, the imaging unit being pivotably arranged in a distal end section of the shaft, a pivot axis of the imaging unit being transverse to a longitudinal axis of the distal end section of the shaft, wherein the image sensor is arranged substantially parallel to an optical axis of the objective lens system, wherein the imaging unit comprises a deflection prism, fixed to an image pick-up surface or a cover glass of the image sensor, for deflecting light exiting from an image end of the objective lens system to the image pick-up surface of the image sensor, wherein the objective lens system and the electronic image sensor are pivotable as a unit with respect to the shaft between a first end position in which the optical axis of the objective lens system is approximately parallel to a longitudinal axis of the distal end section of the shaft and a second end position in which the optical axis of the objective lens system forms a maximal angle, $\alpha$, to the longitudinal axis of the distal end section of the shaft, where $\alpha$ is between approximately 25° and approximately 75°, and wherein a length, L, of the objective lens system is $$L \leq h/\sin \alpha - d/\tan \alpha$$

where h is an inner diameter of the distal end section of the shaft and d is a diameter of the objective lens system.

2. The observation instrument of claim 1, wherein the imaging unit comprises a sleeve holding the objective lens system, and wherein the deflection prism is fixed to an image end of the sleeve.

3. The observation instrument of claim 1, wherein the optical axis of the objective lens system is offset to the image pick-up surface of the image sensor.

4. The observation instrument of claim 1, wherein the pivot axis is arranged at a distal edge of the image sensor.

5. The observation instrument of claim 1, wherein the pivot axis is arranged at a location defined by the intersection of the optical axis of the objective lens system with an entrance face of the deflection prism, the pivot axis being parallel to the image pick-up surface of the image sensor.

6. The observation instrument of claim 1 wherein the pivot axis is arranged at the image end of the objective lens system.

7. The observation instrument of claim 2, wherein the pivot axis is arranged at the image end of the objective lens system.

8. The observation instrument of claim 1, wherein the image sensor has a diagonal having a length exceeding the inner diameter h of the distal end section of the shaft.

9. The observation instrument of claim 2, wherein the image sensor has a diagonal having a length exceeding the inner diameter h of the distal end section of the shaft.

10. The observation instrument of claim 1, wherein the shaft is distally closed by a curved cover glass.

11. The observation instrument of claim 1, wherein the observation instrument is an endoscope, an exoscope or an endoscopic capsule.

12. A video imager arrangement for an observation instrument having a shaft, wherein the video imager arrangement comprises an imaging unit, the imaging unit comprising an objective lens system and an electronic image sensor arranged for picking up an image generated by the objective lens system, the imaging unit being pivotably arrangeable in a distal end section of the shaft, a pivot axis of the imaging unit being transverse to a longitudinal axis of the distal end section of the shaft, characterized in that the image sensor is arranged substantially parallel to an optical axis of the objective lens system and that the imaging unit comprises a deflection prism, fixed to an image pick-up surface or a cover glass of the image sensor, for deflecting light exiting from an image end of the objective lens system to the image pick-up surface of the image sensor, wherein the objective lens system and the electronic image sensor are pivotable as a unit with respect to the shaft between a first end position in which the optical axis of the objective lens system is approximately parallel to a longitudinal axis of the distal end section of the shaft and a second end position in which the optical axis of the objective lens system forms a maximal angle, $\alpha$, to the longitudinal axis of the distal end section of the shaft, where $\alpha$ is between approximately 25° and approximately 75°, and wherein a length, L, of the objective lens system is $$L \leq h/\sin \alpha - d/\tan \alpha$$

where h is an inner diameter of the distal end section of the shaft and d is a diameter of the objective lens system.

13. The video imager arrangement of claim 12, wherein the light deflection element is a deflection prism fixed to the image pick-up surface or cover-glass of the image sensor.

14. The video imager arrangement of claim 13, wherein the imaging unit comprises a sleeve holding the objective lens system, and wherein the deflection prism is fixed to an image end of the sleeve.

* * * * *